（12）United States Patent
Dong et al.

(10) Patent No.: US 8,116,870 B2
(45) Date of Patent: Feb. 14, 2012

(54) CAPTURE DETECTION FOR MULTI-CHAMBER PACING

(75) Inventors: Yanting Dong, Shoreview, MN (US); Scott A. Meyer, Rochester, MN (US); Kevin John Stahlsberg, White Bear Lake, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 855 days.

(21) Appl. No.: 12/214,852

(22) Filed: Jun. 23, 2008

(65) Prior Publication Data

US 2009/0069858 A1    Mar. 12, 2009

Related U.S. Application Data

(63) Continuation of application No. 11/116,563, filed on Apr. 28, 2005, now Pat. No. 7,392,088.

(51) Int. Cl.
*A61N 1/368* (2006.01)
(52) U.S. Cl. .......................................... 607/28
(58) Field of Classification Search ........................ None
See application file for complete search history.

(56) References Cited

U.S. PATENT DOCUMENTS

| | | |
|---|---|---|
| 3,920,005 A | 11/1975 | Gombrich et al. |
| 4,878,497 A | 11/1989 | Callaghan et al. |
| 5,222,493 A | 6/1993 | Sholder |
| 5,271,411 A | 12/1993 | Ripley et al. |
| 5,324,310 A | 6/1994 | Greeninger et al. |
| 5,350,410 A | 9/1994 | Kleks et al. |
| 5,431,693 A | 7/1995 | Schroeppel |
| 5,443,485 A | 8/1995 | Housworth et al. |
| 5,522,860 A | 6/1996 | Molin et al. |
| 5,626,620 A | 5/1997 | Kieval et al. |
| 5,683,431 A | 11/1997 | Wang |
| 5,683,434 A | 11/1997 | Archer |
| 6,101,416 A | 8/2000 | Sloman |
| 6,128,535 A | 10/2000 | Maarse |
| 6,148,234 A | 11/2000 | Struble |
| 6,163,724 A | 12/2000 | Hemming et al. |
| 6,169,921 B1 | 1/2001 | KenKnight et al. |

(Continued)

FOREIGN PATENT DOCUMENTS

EP    0468720    1/1992

(Continued)

OTHER PUBLICATIONS

Notice of Allowance dated Feb. 7, 2008 from U.S. Appl. No. 11/116,563, 4 pages.

(Continued)

*Primary Examiner* — Kennedy Schaetzle
(74) *Attorney, Agent, or Firm* — Hollingsworth & Funk, LLC

(57) ABSTRACT

Multi-chamber pacing may result in capture of one chamber, capture of multiple chambers, fusion, or non-capture. Approaches for detecting various capture conditions during multi-chamber pacing are described. Pacing pulses are delivered to left and right heart chambers during a cardiac cycle. A cardiac electrogram signal is sensed following the delivery of the pacing pulses. Left chamber capture only, right chamber capture only, and bi-chamber capture may be distinguished based on characteristics of the cardiac electrogram signal. Multi-chamber capture detection may be implemented using detection windows having dimensions of time and amplitude. The detection windows are associated with expected features, such as expected signal peaks, under a particular capture condition. The cardiac electrogram signal features are compared to detection windows to determine the capture condition.

24 Claims, 11 Drawing Sheets

U.S. PATENT DOCUMENTS

| | | |
|---|---|---|
| 6,175,766 B1 | 1/2001 | Bornzin et al. |
| 6,192,275 B1 | 2/2001 | Zhu et al. |
| 6,221,011 B1 | 4/2001 | Bardy |
| 6,226,551 B1 | 5/2001 | Zhu et al. |
| 6,238,419 B1 | 5/2001 | Lindgren |
| 6,270,457 B1 | 8/2001 | Bardy |
| 6,275,731 B1 | 8/2001 | Zhu et al. |
| 6,277,072 B1 | 8/2001 | Bardy |
| 6,280,380 B1 | 8/2001 | Bardy |
| RE37,454 E | 11/2001 | Sutton et al. |
| 6,312,378 B1 | 11/2001 | Bardy |
| 6,324,427 B1 | 11/2001 | Florio |
| 6,336,903 B1 | 1/2002 | Bardy |
| 6,345,201 B1 | 2/2002 | Sloman et al. |
| 6,358,203 B2 | 3/2002 | Bardy |
| 6,368,284 B1 | 4/2002 | Bardy |
| 6,398,728 B1 | 6/2002 | Bardy |
| 6,434,428 B1 | 8/2002 | Sloman et al. |
| 6,440,066 B1 | 8/2002 | Bardy |
| 6,449,503 B1 | 9/2002 | Hsu |
| 6,456,881 B1 | 9/2002 | Bornzin et al. |
| 6,466,820 B1 | 10/2002 | Juran et al. |
| 6,477,422 B1 | 11/2002 | Splett |
| 6,493,586 B1 | 12/2002 | Stahmann et al. |
| 6,505,071 B1 | 1/2003 | Zhu et al. |
| 6,512,953 B2 | 1/2003 | Florio et al. |
| 6,567,701 B2 | 5/2003 | Vonk |
| 6,615,082 B1 | 9/2003 | Mandell |
| 6,618,619 B1 | 9/2003 | Florio et al. |
| 6,658,293 B2 | 12/2003 | Vonk |
| 6,738,669 B1 | 5/2004 | Sloman et al. |
| 6,768,924 B2 | 7/2004 | Ding et al. |
| 6,895,274 B2 | 5/2005 | Mower |
| 6,950,702 B2 | 9/2005 | Sweeney |
| 6,973,350 B1 | 12/2005 | Levine et al. |
| 7,006,869 B2 | 2/2006 | Bradley |
| 7,027,868 B2 | 4/2006 | Rueter et al. |
| 7,103,404 B2 | 9/2006 | Staler et al. |
| 7,113,823 B2 | 9/2006 | Yonce et al. |
| 7,177,689 B2 | 2/2007 | Ternes et al. |
| 7,191,003 B2 | 3/2007 | Greenhut et al. |
| 7,191,004 B2 | 3/2007 | Kim et al. |
| 7,286,876 B2 | 10/2007 | Yonce et al. |
| 7,319,900 B2 | 1/2008 | Kim et al. |
| 7,330,761 B2 | 2/2008 | Zhang |
| 7,337,000 B2 | 2/2008 | Meyer et al. |
| 7,392,088 B2 | 6/2008 | Dong |
| 7,477,932 B2 | 1/2009 | Lee et al. |
| 7,529,578 B2 | 5/2009 | Dong et al. |
| 7,558,628 B2 * | 7/2009 | Yonce et al. ............ 607/27 |
| 2001/0049542 A1 | 12/2001 | Florio et al. |
| 2003/0125777 A1 * | 7/2003 | Ding et al. ............ 607/27 |
| 2003/0204214 A1 | 10/2003 | Ferek-Patric |
| 2004/0082975 A1 | 4/2004 | Meyer et al. |
| 2004/0116971 A1 | 6/2004 | Bjorling et al. |
| 2004/0116974 A1 | 6/2004 | Obel |
| 2004/0127951 A1 | 7/2004 | Jarverud et al. |
| 2004/0215277 A1 | 10/2004 | Oosterhoff et al. |
| 2004/0260351 A1 | 12/2004 | Holmstrom et al. |
| 2005/0131477 A1 | 6/2005 | Meyer et al. |
| 2005/0131478 A1 | 6/2005 | Kim et al. |
| 2006/0129196 A1 | 6/2006 | Dong |
| 2006/0241706 A1 | 10/2006 | Yonce et al. |
| 2006/0247695 A1 | 11/2006 | Stalsberg et al. |
| 2007/0255329 A1 * | 11/2007 | Bjorling ............ 607/28 |
| 2008/0154324 A1 | 6/2008 | Kim |
| 2009/0069858 A1 | 3/2009 | Dong |

FOREIGN PATENT DOCUMENTS

| | | |
|---|---|---|
| EP | 1291038 | 3/2003 |
| EP | 1430930 | 6/2004 |
| JP | 6502778 | 3/1994 |
| WO | WO 2004026398 | 4/2004 |
| WO | WO 2005058412 | 6/2005 |

OTHER PUBLICATIONS

Office Action Response dated Oct. 29, 2007 from U.S. Appl. No. 11/116,563, 11 pages.

Office Action dated Jul. 27, 2007 from U.S. Appl. No. 11/116,563, 7 pages.

Office Action Response dated Apr. 26, 2007 from U.S. Appl. No. 11/116,563, 13 pages.

Office Action dated Jan. 26, 2007 from U.S. Appl. No. 11/116,563, 11 pages.

Notice of Allowance dated Mar. 29, 2010 from U.S. Appl. No. 11/010,973, 4 pages.

Office Action Response dated Feb. 17, 2010 from U.S. Appl. No. 11/010,973, 13 pages.

Office Action dated Nov. 20, 2009 from U.S. Appl. No. 11/010,973, 8 pages.

Office Action Response dated Sep. 10, 2009 from U.S. Appl. No. 11/010,973, 12 pages.

Interview Summary dated Aug. 27, 2009 from U.S. Appl. No. 11/010,973, 4 pages.

Office Action dated Jul. 23, 2009 from U.S. Appl. No. 11/010,973, 10 pages.

Office Action Response dated Jun. 30, 2009 from U.S. Appl. No. 11/010,973, 12 pages.

Interview Summary dated Jun. 29, 2009 from U.S. Appl. No. 11/010,973, 2 pages.

Office Action dated May 5, 2009 from U.S. Appl. No. 11/010,973, 11 pages.

Office Action Response dated Feb. 3, 2009 from U.S. Appl. No. 11/010,973, 13 pages.

Office Action dated Nov. 5, 2008 from U.S. Appl. No. 11/010,973, 9 pages.

Notice of Allowance dated Apr. 28, 2008 from U.S. Appl. No. 11/010,973, 8 pages.

Office Action Response dated Jan. 24, 2008 from U.S. Appl. No. 11/010,973, 15 pages.

Office Action dated Sep. 24, 2007 from U.S. Appl. No. 11/010,973, 7 pages.

International Preliminary Report on Patentability dated Oct. 30, 2007 from PCT Application No. PCT/US2006/016196, 8 pages.

International Search Report and Written Opinion dated Sep. 25, 2006 from PCT Application No. PCT/US2006/016196, 14 pages.

International Preliminary Report on Patentability dated Jun. 21, 2007 from PCT Application No. PCT/US2005/045029, 9 pages.

International Search Report and Written Opinion dated May 24, 2006 from PCT Application No. PCT/US2005/045029, 12 pages.

Notice of Allowance dated Dec. 30, 2008 from U.S. Appl. No. 11/180,937, 6 pages.

Sep. 17, 2008, Office Action Response dated Jan. 24, 2008 from U.S. Appl. No. 11/180,937, 12 pages.

Office Action dated Jun. 17, 2008 from U.S. Appl. No. 11/180,937, 12 pages.

Splett et al., Determination of Pacing Capture in Implantable Defibrillators: Benefit of Evoked Response Detection Using RV Coil to Can Vector, PACE, vol. 23, pp. 1645-1650, Nov. 23, 2000.

Office Action dated Sep. 23, 2010 from European application No. 05853855.4, 4 pages.

Jul. 28, 2011, File History for U.S. Appl. No. 11/180,937.

Office Action dated Jul. 12, 2011 for JP Application No. 2007-546821, 2 pages.

Office Action with translation dated Nov. 2, 2011 for JP Application No. 2008-509164, 5 pages.

* cited by examiner

CAPTURE DETECTION FOR MULTI-CHAMBER PACING

RELATED PATENT DOCUMENTS

This application is a continuation of U.S. patent application Ser. No. 11/116,563 filed on Apr. 28, 2005, which is incorporated herein by reference in its entirety.

FIELD OF THE INVENTION

The present invention relates generally to cardiac devices and methods, and, more particularly, to cardiac devices and methods used in detecting capture in multi-chamber pacing.

BACKGROUND OF THE INVENTION

When functioning normally, the heart produces rhythmic contractions and is capable of pumping blood throughout the body. The heart has specialized conduction pathways in both the atria and the ventricles that enable the rapid conduction of excitation impulses (i.e. depolarizations) from the SA node throughout the myocardium. These specialized conduction pathways conduct the depolarizations from the SA node to the atrial myocardium, to the atrioventricular node, and to the ventricular myocardium to produce a coordinated contraction of both atria and both ventricles.

The conduction pathways synchronize the contractions of the muscle fibers of each chamber as well as the contraction of each atrium or ventricle with the opposite atrium or ventricle. Without the synchronization afforded by the normally functioning specialized conduction pathways, the heart's pumping efficiency is greatly diminished. Patients who exhibit pathology of these conduction pathways can suffer compromised cardiac output.

Cardiac rhythm management devices have been developed that provide pacing stimulation to one or more heart chambers in an attempt to improve the rhythm and coordination of atrial and/or ventricular contractions. Cardiac rhythm management devices typically include circuitry to sense signals from the heart and a pulse generator for providing electrical stimulation to the heart. Leads extending into the patient's heart chamber and/or into veins of the heart are coupled to electrodes that sense the heart's electrical signals and for delivering stimulation to the heart in accordance with various therapies for treating cardiac arrhythmias.

Pacemakers are cardiac rhythm management devices that deliver a series of low energy pace pulses timed to assist the heart in producing a contractile rhythm that maintains cardiac pumping efficiency. Pace pulses may be intermittent or continuous, depending on the needs of the patient. There exist a number of categories of pacemaker devices, with various modes for sensing and pacing one or more heart chambers.

A pace pulse must exceed a minimum energy value, or capture threshold, to produce a contraction. It is desirable for a pace pulse to have sufficient energy to stimulate capture of the heart chamber without expending energy significantly in excess of the capture threshold. Thus, accurate determination of the capture threshold is required for efficient pace energy management. If the pace pulse energy is too low, the pace pulses may not reliably produce a contractile response in the heart chamber and may result in ineffective pacing. If the pace pulse energy is too high, the patient may experience discomfort and the battery life of the device will be shorter.

Detecting if a pacing pulse "captures" the heart and produces a contraction allows the pacemaker to adjust the energy level of pace pulses to correspond to the optimum energy expenditure that reliably produces capture. Further, capture detection allows the pacemaker to initiate a back-up pulse at a higher energy level whenever a pace pulse does not produce a contraction.

When a pace pulse produces a contraction in the heart chamber, the electrical cardiac signal preceding the contraction is denoted the captured response. The captured response typically includes an electrical signal, denoted the evoked response signal, associated with the heart contraction, along with a superimposed signal associated with residual post pace polarization at the electrode-tissue interface. The magnitude of the residual post pace polarization signal, or pacing artifact, may be affected by a variety of factors including lead polarization, after-potential from the pace pulse, lead impedance, patient impedance, pace pulse width, and pace pulse amplitude, for example. The evoked response may be affected by interaction with intrinsic heart activity and resulting in a fusion or pseudofusion response.

Multi-chamber pacemakers may include electrodes positioned to contact cardiac tissue within or adjacent to both the left and the right ventricles for pacing both the left and right ventricles. This type of device allows bi-ventricular pacing therapy to be applied, for example, to coordinate ventricular contractions when a patient suffers from congestive heart failure (CHF). Furthermore, multi-chamber pacemakers may include electrodes positioned to contact tissue within or adjacent to both the left and the right atria to enable bi-atrial pacing.

It is desirable to determine if pacing pulses delivered to multiple heart chambers produce a captured response in one, both, or none of the paced chambers. The present invention provides methods and systems used for enhancing the discrimination of the cardiac response to multi-chamber pacing and provides various advantages over the prior art.

SUMMARY OF THE INVENTION

The present invention involves approaches for detecting various capture conditions during multi-chamber pacing. One embodiment of the invention involves a method for detection various capture conditions. Pacing pulses are delivered to left and right heart chambers during a cardiac cycle. A cardiac electrogram signal is sensed following the delivery of the pacing pulses. The method includes distinguishing between left chamber capture only, right chamber capture only, and bi-chamber capture based on characteristics of the cardiac electrogram signal.

According to one aspect, the pacing pulses are delivered to left and right ventricles. The method includes distinguishing between left ventricular capture only, right ventricular capture only, and bi-ventricular capture.

The cardiac electrogram signal may be sensed, for example, using an electrode positioned in, on or within a vein of the right heart chamber, using an electrode positioned in, on, or within a vein of the left heart chamber or using both left heart chamber and right heart chamber electrodes.

In one implementation, each of the templates, comprising detection windows having dimensions of time and amplitude, are associated with left chamber capture, right chamber capture, or bi-chamber capture. The cardiac electrogram signal is compared to one or more of the templates to determine the type of capture condition. The detection windows are associated with an expected feature, e.g., peaks, of the cardiac electrogram under a particular capture condition.

Another embodiment of the invention involves a cardiac device. The cardiac device includes a sensing channel configured to sense a cardiac electrogram signal following delivery of pacing pulses delivered to left and right heart chambers, respectively, during a cardiac cycle. A processor coupled to the sensing circuitry, the processor configured to distinguish between left chamber capture only, right chamber capture only, and bi-chamber capture based on characteristics of the cardiac signal.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

Figure 1:
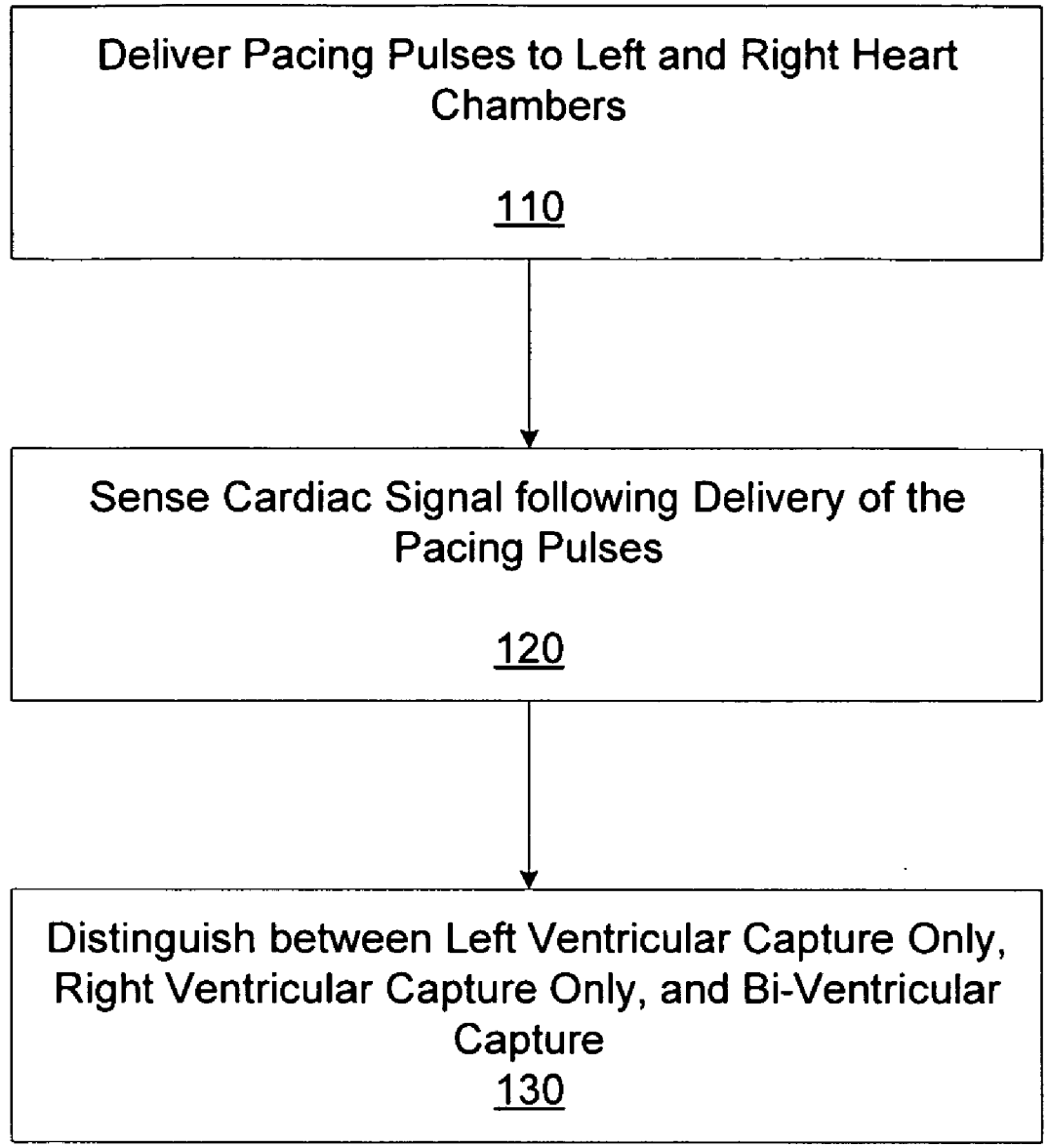
FIG. 1 is a flowchart illustrating a method of capture detection in accordance with embodiments of the invention.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings forming a part hereof, and in which are shown by way of illustration, various embodiments by which the invention may be practiced. It is to be understood that other embodiments may be utilized, and structural and functional changes may be made without departing from the scope of the present invention.

A pacemaker or other cardiac rhythm management device may determine whether an applied electrical pacing stimulus captures a heart chamber. The systems and methods described herein involve the use of features of a cardiac electrogram to discriminate between various types of cardiac responses to multi-chamber pacing. The approaches of the present invention provide for enhanced capture threshold testing and/or beat to beat automatic capture verification for multi-chamber pacing, for example.

Several functions of cardiac devices rely on the heart response consistency. For example, automatic capture threshold testing and/or automatic capture verification algorithms may rely on templates of the heart's response as the basis for determining whether a future pacing stimulus produces a particular type of response. Templates representative of various types of cardiac responses may comprise one or more detection windows. The detection windows are compared to a cardiac signal following delivery of multi-chamber pacing. In multi-chamber pacing, pacing pulses delivered to two opposite, i.e., left and right, heart chambers during a cardiac cycle. In accordance with embodiments of the invention, the cardiac signal following pacing is analyzed to discriminate, for example between left heart chamber capture, right heart chamber capture, multi-chamber capture, fusion and non-capture.

FIG. 1 is a flowchart illustrating a method of multi-chamber capture detection in accordance with embodiments of the invention. Pacing pulses are delivered 110 to left and right heart chambers during a cardiac cycle. For example, a pacing pulse may be delivered to the left ventricle (LV) and to the right ventricle (RV). The pacing pulses may be delivered over separate pacing channels and may be delivered substantially simultaneously or may be separated in time by an interventricular delay (IVD). The cardiac signal following delivery of the pacing pulses is sensed 120. The cardiac signal may be sensed, for example, using an evoked response sensing channel that is configured for detection of the cardiac response to the multi-chamber pacing. The cardiac response to the multi-chamber pacing is determined based on characteristics of the sensed cardiac signal. Capture of the left chamber only, right chamber only, multi-chamber capture, fusion or non-capture may be discriminated 130.

The embodiments of the present system illustrated herein are generally described as being implemented in a patient implantable medical device (PIMD) such as a pacemaker/defibrillator (PD) that may operate in numerous pacing modes known in the art. Various types of multiple chamber implantable cardiac pacemaker/defibrillators are known in the art and may be used in connection with cardiac devices and methods that provide multi-chamber capture detection in accordance with the approaches of the present invention. The methods of the present invention may be implemented in a variety of implantable or patient-external cardiac rhythm management devices, including multi-chamber pacemakers, defibrillators, cardioverters, bi-ventricular pacemakers, cardiac resynchronizers, and cardiac monitoring systems, for example.

A device suitable for implementing the capture detection methods of the present invention may include stimulation circuitry from delivering stimulation pulses to the heart and includes sensing circuitry comprising electrodes electrically coupled to the heart. Leads from the sensing and/or stimulation circuitry are coupled to electrodes positioned within heart chambers, positioned within veins of the heart, and/or positioned on the heart. The electrodes sense the heart's electrical signals, which are denoted cardiac electrogram signals. Each lead may include multiple electrodes, and each electrode may be used to sense a separate electrogram signal for capture detection.

Although the present system is described in conjunction with an implantable cardiac pacemaker/defibrillator having a microprocessor-based architecture, it will be understood that the implantable pacemaker/defibrillator (or other device) may be implemented using any logic-based circuit architecture, if desired.

Figure 2:
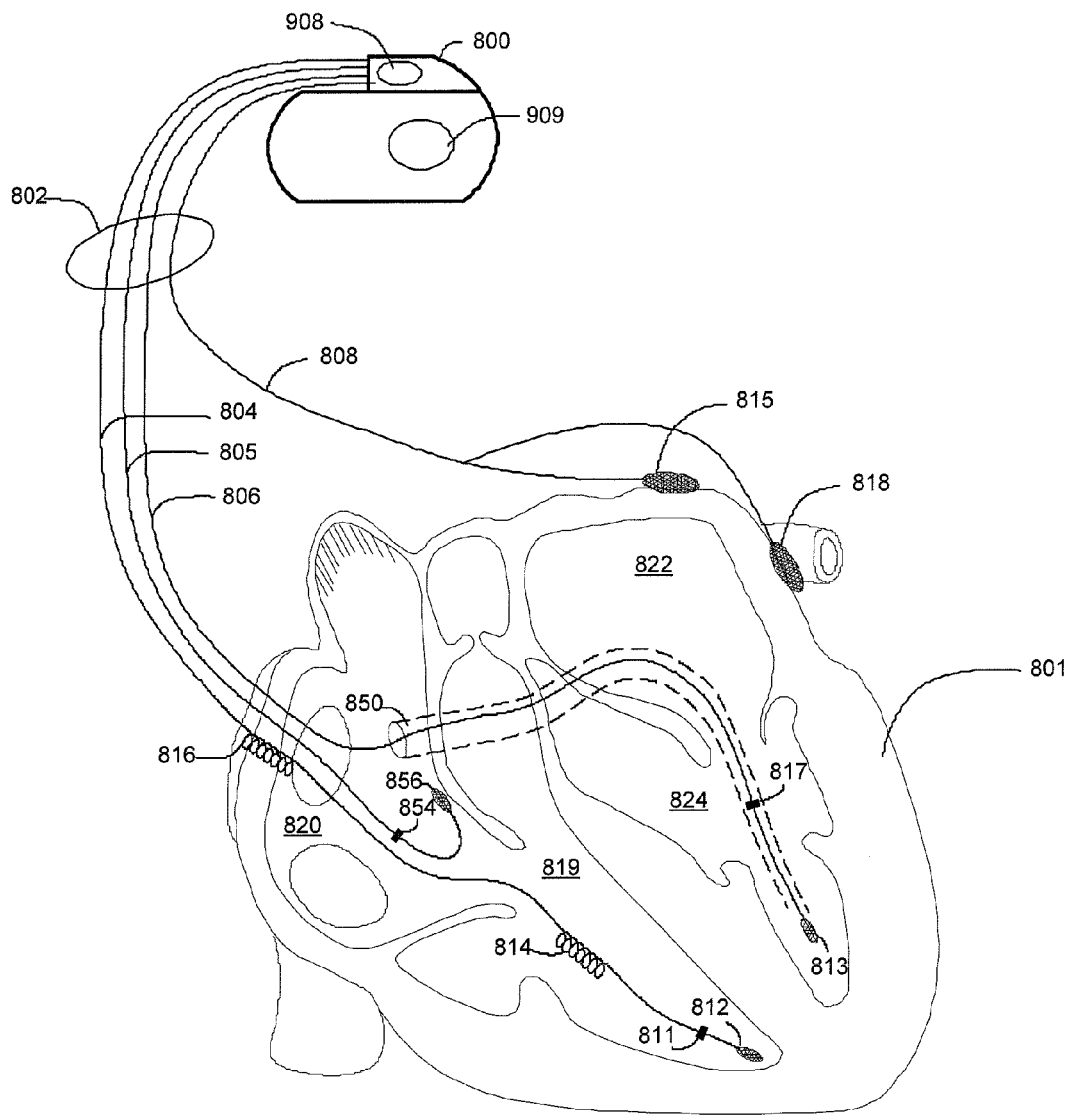
FIG. 2 is a partial view of one embodiment of an implantable medical device suitable for implementing multi-chamber capture detection in accordance with embodiments of the invention.

Referring now to FIG. 2 of the drawings, there is shown a partial view of a cardiac rhythm management device that may be used to implement multi-chamber capture detection in accordance with the present invention. The cardiac rhythm management device in FIG. 2 includes a pacemaker/defibrillator 800 electrically and physically coupled to a lead system 802. The housing and/or header of the pacemaker/defibrillator 800 may incorporate one or more electrodes 908, 909 used to provide electrical stimulation energy to the heart and to sense cardiac electrical activity. The pacemaker/defibrillator 800 may utilize all or a portion of the pacemaker/defibrillator housing as a can electrode 909. The pacemaker/defibrillator 800 may include an indifferent electrode 908 positioned, for example, on the header or the housing of the pacemaker/defibrillator 800. If the pacemaker/defibrillator 800 includes both a can electrode 909 and an indifferent electrode 908, the electrodes 908, 909 typically are electrically isolated from each other.

The lead system 802 is used to detect electric cardiac signals produced by the heart 801 and to provide electrical energy to the heart 801 under certain predetermined conditions to treat cardiac arrhythmias. The lead system 802 may include one or more electrodes used for pacing, sensing, and/or defibrillation. In the embodiment shown in FIG. 2, the lead system 802 includes an intracardiac right ventricular (RV) lead system 804, an intracardiac right atrial (RA) lead system 805, an intracardiac left ventricular (LV) lead system 806, and an extracardiac left atrial (LA) lead system 808. The lead system 802 of FIG. 2 illustrates one embodiment that may be used in connection with the multi-chamber capture detection methodologies described herein. Other leads and/or electrodes may additionally or alternatively be used.

The lead system 802 may include intracardiac leads 804, 805, 806 implanted in a human body with portions of the intracardiac leads 804, 805, 806 inserted into a heart 801. The intracardiac leads 804, 805, 806 include various electrodes positionable within the heart for sensing electrical activity of the heart and for delivering electrical stimulation energy to the heart, for example, pacing pulses and/or defibrillation shocks to treat various arrhythmias of the heart.

As illustrated in FIG. 2, the lead system 802 may include one or more extracardiac leads 808 having electrodes, e.g., epicardial electrodes, positioned at locations outside the heart for sensing and pacing one or more heart chambers.

The right ventricular lead system 804 illustrated in FIG. 2 includes an SVC-coil 816, an RV-coil 814, an RV-ring electrode 811, and an RV-tip electrode 812. The right ventricular lead system 804 extends through the right atrium 820 and into the right ventricle 819. In particular, the RV-tip electrode 812, RV-ring electrode 811, and RV-coil electrode 814 are positioned at appropriate locations within the right ventricle 819 for sensing and delivering electrical stimulation pulses to the heart 801. The SVC-coil 816 is positioned at an appropriate location within the right atrium chamber 820 of the heart 801 or a major vein leading to the right atrial chamber 820 of the heart 801.

In one configuration, the RV-tip electrode 812 referenced to the can electrode 909 may be used to implement unipolar pacing and/or sensing in the right ventricle 819. Bipolar pacing and/or sensing in the right ventricle may be implemented using the RV-tip 812 and RV-ring 811 electrodes. In yet another configuration, the RV-ring 811 electrode may optionally be omitted, and bipolar pacing and/or sensing may be accomplished using the RV-tip electrode 812 and the RV-coil 814, for example. The RV-coil 814 and the SVC-coil 816 are defibrillation electrodes.

The left ventricular lead 806 includes an LV distal electrode 813 and an LV proximal electrode 817 located at appropriate locations in or about the left ventricle 824 for pacing and/or sensing the left ventricle 824. The left ventricular lead 806 may be guided into the right atrium 820 of the heart via the superior vena cava. From the right atrium 820, the left ventricular lead 806 may be deployed into the coronary sinus ostium, the opening of the coronary sinus 850. The lead 806 may be guided through the coronary sinus 850 to a coronary vein of the left ventricle 824. This vein is used as an access pathway for leads to reach the surfaces of the left ventricle 824 which are not directly accessible from the right side of the heart. Lead placement for the left ventricular lead 806 may be achieved via subclavian vein access and a preformed guiding catheter for insertion of the LV electrodes 813, 817 adjacent to the left ventricle.

Unipolar pacing and/or sensing in the left ventricle may be implemented, for example, using the LV distal electrode referenced to the can electrode 909. The LV distal electrode 813 and the LV proximal electrode 817 may be used together as bipolar sense and/or pace electrodes for the left ventricle. The left ventricular lead 806 and the right ventricular lead 804, in conjunction with the pacemaker/defibrillator 800, may be used to provide cardiac resynchronization therapy such that the ventricles of the heart are paced substantially simultaneously, or in phased sequence, to provide enhanced cardiac pumping efficiency for patients suffering from chronic heart failure.

The right atrial lead 805 includes a RA-tip electrode 856 and an RA-ring electrode 854 positioned at appropriate locations in the right atrium 820 for sensing and pacing the right atrium 820. In one configuration, the RA-tip 856 referenced to the can electrode 909, for example, may be used to provide unipolar pacing and/or sensing in the right atrium 820. In another configuration, the RA-tip electrode 856 and the RA-ring electrode 854 may be used to provide bipolar pacing and/or sensing.

FIG. 2 illustrates one embodiment of a left atrial lead system 808. In this example, the left atrial lead 808 is implemented as an extracardiac lead with LA distal 818 and LA proximal 815 electrodes positioned at appropriate locations outside the heart 801 for sensing and pacing the left atrium 822. Unipolar pacing and/or sensing of the left atrium may be accomplished, for example, using the LA distal electrode 818 to the can 909 pacing vector. The LA proximal 815 and LA distal 818 electrodes may be used together to implement bipolar pacing and/or sensing of the left atrium 822. The right atrial lead 805 and the left atrial lead 808 may be used in conjunction with the pacemaker/defibrillator 800 to provide bi-atrial pacing.

Figure 3:
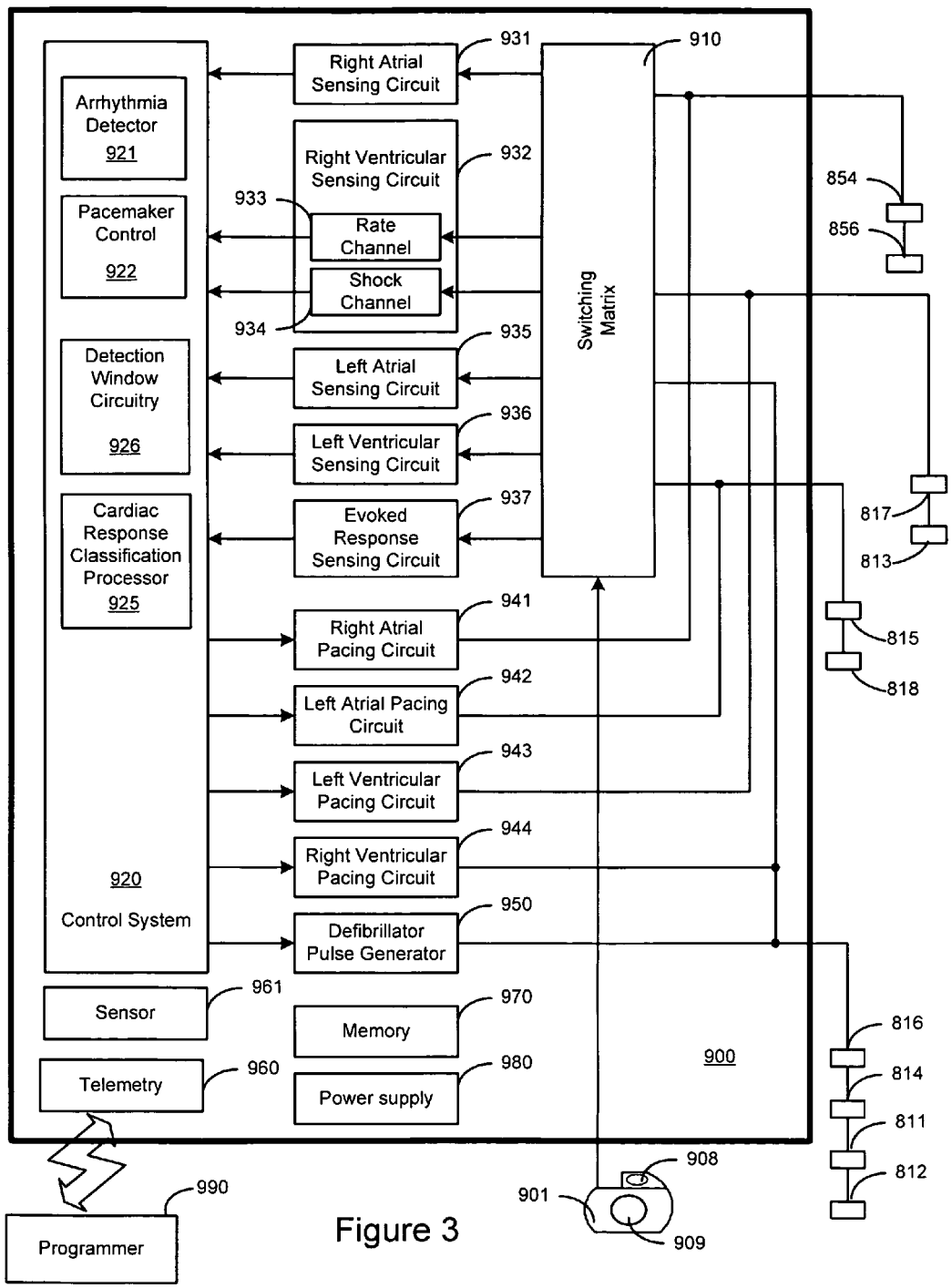
FIG. 3 is a block diagram of an implantable medical device suitable for implementing multi-chamber capture detection in accordance with embodiments of the invention.

Referring now to FIG. 3, there is shown a block diagram of a cardiac pacemaker/defibrillator 900 suitable for implementing multi-chamber capture detection methods of the present invention. FIG. 3 shows a cardiac pacemaker/defibrillator 900 divided into functional blocks. It is understood by those skilled in the art that there exist many possible configurations in which these functional blocks can be arranged. The example depicted in FIG. 3 is one possible functional arrangement. Other arrangements are also possible. For example, more, fewer or different functional blocks may be used to describe a cardiac pacemaker/defibrillator suitable for implementing the methodologies for multi-chamber capture detection in accordance with the present invention. In addition, although the cardiac pacemaker/defibrillator 900 depicted in FIG. 3 contemplates the use of a programmable microprocessor-based logic circuit, other circuit implementations may be utilized.

The cardiac pacemaker/defibrillator 900 depicted in FIG. 3 includes circuitry for receiving cardiac signals from a heart and delivering electrical stimulation energy to the heart in the form of pacing pulses or defibrillation shocks. In one embodiment, the circuitry of the cardiac pacemaker/defibrillator 900 is encased and hermetically sealed in a housing 901 suitable for implanting in a human body. Power to the cardiac pacemaker/defibrillator 900 is supplied by an electrochemical battery 980. A connector block (not shown) is attached to the housing 901 of the cardiac pacemaker/defibrillator 900 to allow for the physical and electrical attachment of the lead system conductors to the circuitry of the cardiac pacemaker/defibrillator 900.

The cardiac pacemaker/defibrillator 900 may be a programmable microprocessor-based system, including a control system 920 and a memory 970. The memory 970 may store parameters for various pacing, defibrillation, and sensing modes, along with other parameters. Further, the memory 970 may store data indicative of cardiac signals received by other components of the cardiac pacemaker/defibrillator 900. The memory 970 may be used, for example, for storing historical cardiac electrogram and therapy data. The historical data storage may include, for example, data obtained from long-term patient monitoring used for trending and/or other diagnostic purposes. Historical data, as well as other information, may be transmitted to an external programmer unit 990 as needed or desired.

The control system 920 and memory 970 may cooperate with other components of the cardiac pacemaker/defibrillator 900 to control the operations of the cardiac pacemaker/defibrillator 900. The control system 920 depicted in FIG. 3 incorporates detection window circuitry 926 configured to provide multi-chamber capture detection as described herein.

The control system 920 further includes a cardiac response classification processor 925 that works in conjunction with the detection window circuitry 926. The cardiac response classification processor 925 performs the function of analyzing the location of cardiac signal features with respect to one or more detection windows to determine the cardiac response to pacing.

The control system 920 may include additional functional components including a pacemaker control circuit 922, an arrhythmia detector 921, along with other components for controlling the operations of the cardiac pacemaker/defibrillator 900.

Telemetry circuitry 960 may be implemented to provide communications between the cardiac pacemaker/defibrillator 900 and an external programmer unit 990. In one embodiment, the telemetry circuitry 960 and the programmer unit 990 communicate using a wire loop antenna and a radio frequency telemetric link, as is known in the art, to receive and transmit signals and data between the programmer unit 990 and the telemetry circuitry 960. In this manner, programming commands and other information may be transferred to the control system 920 of the cardiac pacemaker/defibrillator 900 from the programmer unit 990 during and after implant. In addition, stored cardiac data pertaining to capture threshold, capture detection and/or cardiac response classification, for example, along with other data, may be transferred to the programmer unit 990 from the cardiac pacemaker/defibrillator 900.

The telemetry circuitry 960 may provide for communication between the cardiac pacemaker/defibrillator 900 and an advanced patient management (APM) system. The advanced patient management system allows physicians or other personnel to remotely and automatically monitor cardiac and/or other patient conditions. In one example, a cardiac pacemaker/defibrillator, or other device, may be equipped with various telecommunications and information technologies that enable real-time data collection, diagnosis, and treatment of the patient. Various embodiments described herein may be used in connection with advanced patient management.

Methods, structures, and/or techniques described herein, which may be adapted to provide for remote patient/device monitoring, diagnosis, therapy, or other APM related methodologies, may incorporate features of one or more of the following references: U.S. Pat. Nos. 6,221,011; 6,270,457; 6,277,072; 6,280,380; 6,312,378; 6,336,903; 6,358,203; 6,368,284; 6,398,728; and 6,440,066, which are hereby incorporated herein by reference.

In the embodiment of the cardiac pacemaker/defibrillator 900 illustrated in FIG. 3, electrodes RA-tip 856, RA-ring 854, RV-tip 812, RV-ring 811, RV-coil 814, SVC-coil 816, LV distal electrode 813, LV proximal electrode 817, LA distal electrode 818, LA proximal electrode 815, indifferent electrode 908, and can electrode 909 are coupled through a switch matrix 910 to sensing circuits 931-937.

A right atrial sensing circuit 931 serves to detect and amplify electrical signals from the right atrium of the heart. Bipolar sensing in the right atrium may be implemented, for example, by sensing voltages developed between the RA-tip 856 and the RA-ring 854. Unipolar sensing may be implemented, for example, by sensing voltages developed between the RA-tip 856 and the can electrode 909. Outputs from the right atrial sensing circuit are coupled to the control system 920.

A right ventricular sensing circuit 932 serves to detect and amplify electrical signals from the right ventricle of the heart. The right ventricular sensing circuit 932 may include, for example, a right ventricular rate channel 933 and a right ventricular shock channel 934. Right ventricular cardiac signals sensed through use of the RV-tip 812 electrode are right ventricular near-field signals and are denoted RV rate channel signals. A bipolar RV rate channel signal may be sensed as a voltage developed between the RV-tip 812 and the RV-ring 811. Alternatively, bipolar sensing in the right ventricle may be implemented using the RV-tip electrode 812 and the RV-coil 814. Unipolar rate channel sensing in the right ventricle may be implemented, for example, by sensing voltages developed between the RV-tip 812 and the can electrode 909.

Right ventricular cardiac signals sensed through use of the defibrillation electrodes are far-field signals, also referred to as RV morphology or RV shock channel signals. More particularly, a right ventricular shock channel signal may be detected as a voltage developed between the RV-coil 814 and the SVC-coil 816. A right ventricular shock channel signal may also be detected as a voltage developed between the RV-coil 814 and the can electrode 909. In another configuration the can electrode 909 and the SVC-coil electrode 816 may be electrically shorted and a RV shock channel signal may be detected as the voltage developed between the RV-coil 814 and the can electrode 909/SVC-coil 816 combination.

Left atrial cardiac signals may be sensed through the use of one or more left atrial electrodes 815, 818, which may be configured as epicardial electrodes. A left atrial sensing circuit 935 serves to detect and amplify electrical signals from the left atrium of the heart. Bipolar sensing and/or pacing in the left atrium may be implemented, for example, using the LA distal electrode 818 and the LA proximal electrode 815. Unipolar sensing and/or pacing of the left atrium may be accomplished, for example, using the LA distal electrode 818 to can vector 909 or the LA proximal electrode 815 to can vector 909.

A left ventricular sensing circuit 936 serves to detect and amplify electrical signals from the left ventricle of the heart. Bipolar sensing in the left ventricle may be implemented, for example, by sensing voltages developed between the LV distal electrode 813 and the LV proximal electrode 817. Unipolar sensing may be implemented, for example, by sensing voltages developed between the LV distal electrode 813 or the LV proximal electrode 817 and the can electrode 909.

Optionally, an LV coil electrode (not shown) may be inserted into the patient's cardiac vasculature, e.g., the coronary sinus, adjacent the left heart. Signals detected using combinations of the LV electrodes, 813, 817, LV coil electrode (not shown), and/or can electrodes 909 may be sensed and amplified by the left ventricular sensing circuitry 936. The output of the left ventricular sensing circuit 936 is coupled to the control system 920.

The outputs of the switching matrix 910 may be operated to couple selected combinations of electrodes 811, 812, 813, 814, 815, 816, 817, 818, 856, 854 to an evoked response sensing circuit 937. The evoked response sensing circuit 937 serves to sense and amplify signals developed using various combinations of electrodes for discrimination of various cardiac responses to pacing in accordance with embodiments of the invention. The cardiac response classification processor 925 may cooperate with detection window circuitry 926 to analyze the output of the evoked response sensing circuit 937 for implementation of multi-chamber cardiac pacing response classification.

Various combinations of pacing and sensing electrodes may be utilized in connection with pacing and sensing the cardiac signal following the pace pulses to determine the cardiac response to the pacing pulse. The pacemaker control circuit 922, in combination with pacing circuitry for the left atrium, right atrium, left ventricle, and right ventricle 941, 942, 943, 944, may be implemented to selectively generate and deliver pacing pulses to the heart using various electrode combinations. The pacing electrode combinations may be used to effect bipolar or unipolar pacing pulses to a heart chamber using one of the pacing vectors as described above.

In some implementations, the cardiac pacemaker/defibrillator 900 may include a sensor 961 that is used to sense the patient's hemodynamic need. In one implementation, the sensor may comprise, for example, an accelerometer configured to sense patient activity. In another implementation, the sensor may comprise an impedance sensor configured to sense patient respiration. The pacing output of the cardiac pacemaker/defibrillator may be adjusted based on the sensor output.

The electrical signal following the delivery of the pacing pulses may be sensed through various sensing vectors coupled through the switch matrix 910 to the evoked response sensing circuit 937 and/or other sensing circuits and used to classify the cardiac response to pacing. The cardiac response may be classified as one of left chamber capture only, right chamber capture only, multi-chamber capture, fusion and non-capture, for example.

Subcutaneous electrodes may provide additional sensing vectors useable for cardiac response classification. In one implementation, cardiac rhythm management system may involve a hybrid system including an intracardiac device configured to pace the heart and an extracardiac device, e.g., a subcutaneous defibrillator, configured to perform functions other than pacing. The extracardiac device may be employed to detect and classify cardiac response to pacing based on signals sensed using subcutaneous electrode arrays. The extracardiac and intracardiac devices may operate cooperatively with communication between the devices occurring over a wireless link, for example. Examples of subcutaneous electrode systems and devices are described in commonly owned U.S. Publication Nos. 2004/0230229 and 2004/0230230, which are hereby incorporated herein by reference in their respective entireties.

Figure 4A:
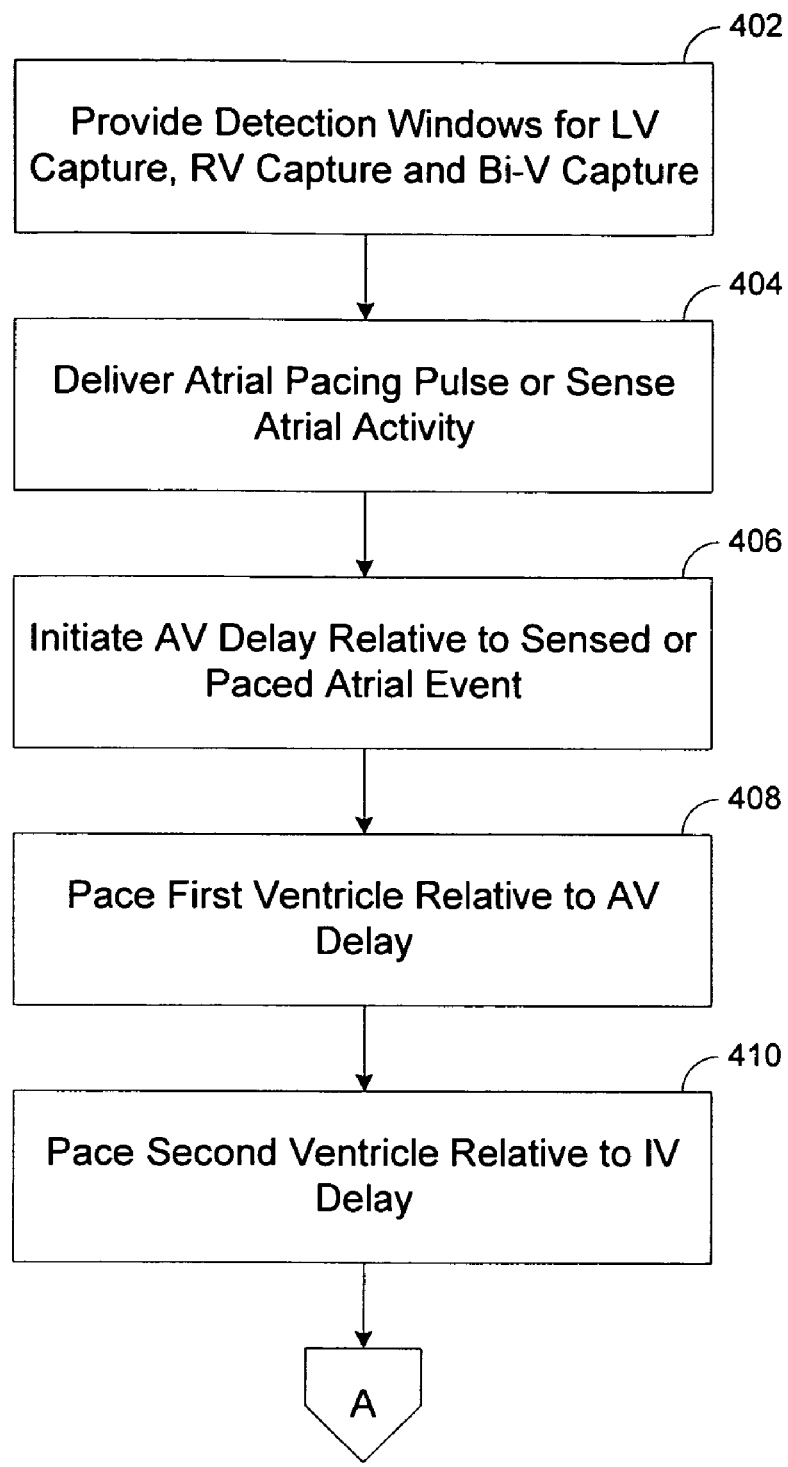
FIGS. 4A and 4B provide a flowchart illustrating a method of bi-ventricular capture detection in accordance with embodiments of the invention.
Figure 4B:
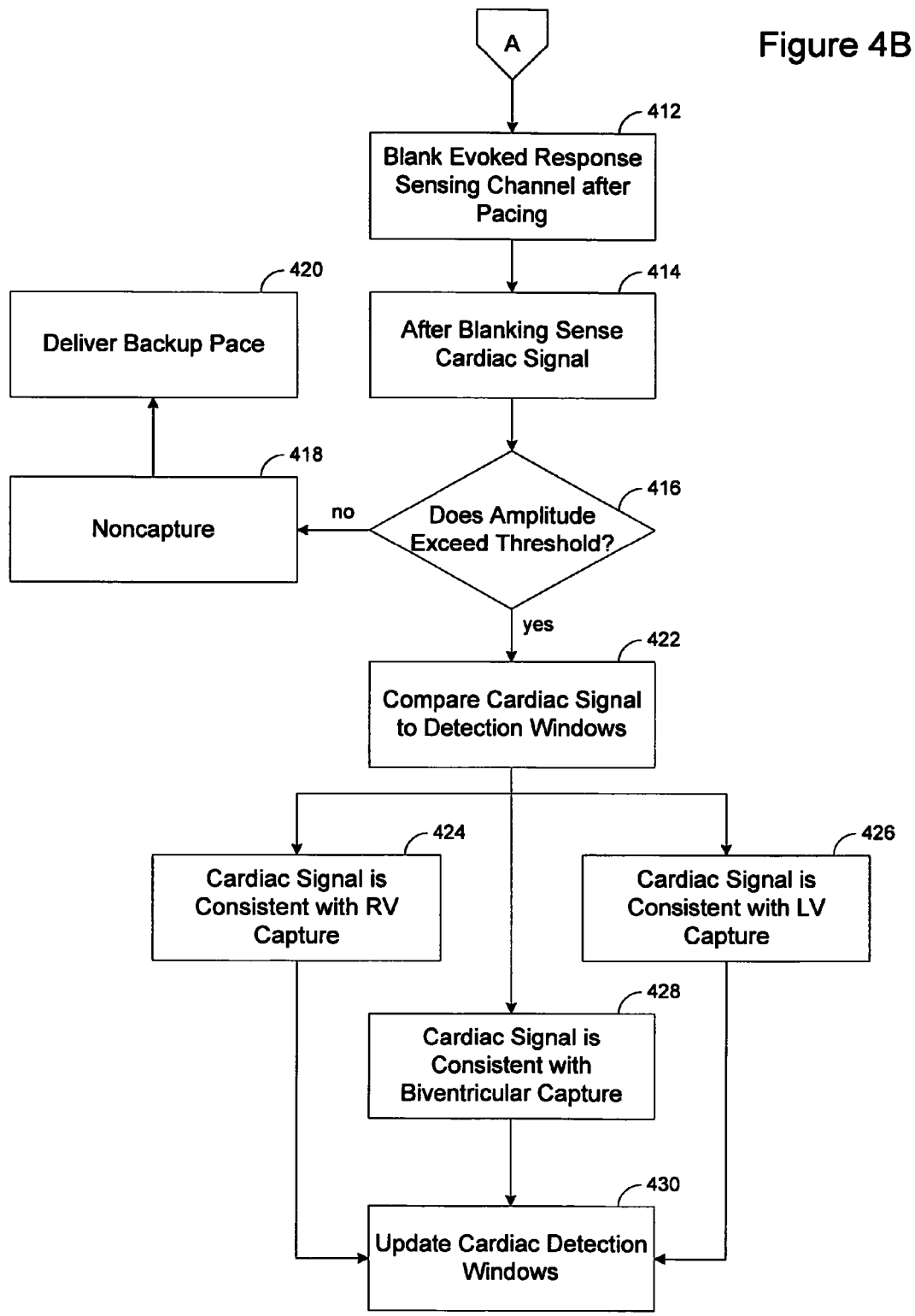

FIG. 4 is a flowchart illustrating a multi-chamber capture method in accordance with the present invention as applied to a bi-ventricular pacing embodiment. Detection windows are provided 402, each detection window corresponding to an expected feature of the cardiac signal under conditions of LV capture, RV capture or bi-ventricular capture. The detection windows may be provided based on clinical data taken from a number of patients or may be formed based on data taken from the patient.

In one implementation, detection windows associated with a particular capture condition may be formed by measuring a number of cardiac signals of the patient under the particular capture condition, extracting one or more features from each of the cardiac signals, clustering the features, and determining detection window boundaries based on the clustered features. In one implementation, the features extracted and clustered comprise positive and negative cardiac signal peaks. Forming detection windows based on clustering is described in commonly owned U.S. Pat. No. 7,499,751, which is hereby incorporated herein by reference. The one or more detection windows used for detecting the particular capture condition form a detection template. Detection windows and templates comprising one or more detection windows for each capture condition (LV capture, RV capture, and bi-ventricular capture) may be formed using the clustering approach or other methods.

In some cases, pacing the ventricles based on tracked atrial events is used to more closely mimic the patient's natural rhythm. During a cardiac cycle, an atrial pacing pulse is delivered to the atrium or atrial activity is sensed 404. An atrioventricular (AV) delay is initiated 406 relative to the sensed or paced atrial event. The AV delay may have a predetermined, programmable, or automatically adjustable duration.

Maintaining consistent bi-ventricular pacing enhances cardiac resynchronization. The AV delay may be set to a relatively short duration relative to the patient's AV conduction time to promote bi-ventricular pacing.

The first and second ventricles may be paced substantially simultaneously or in phased sequence. In one implementation, a first ventricle (left or right) is paced 408 relative to the AV delay and the second ventricle (right or left) is paced 410 relative an interventricular (IV) delay. The interventricular delay may be a fixed, programmable, or automatically adjustable duration.

The sensing channel used for capture detection, e.g., evoked response channel, is blanked 412 after the ventricular paces. For example, the evoked response channel may be blanked during the interventricular delay and for about 0 milliseconds to about 40 milliseconds after the last ventricular pace. After blanking, the cardiac signal is sensed 414. The cardiac signal comprises a cardiac electrogram signal that may be sensed using one or more electrodes positioned within one or more heart chambers and/or within one or more veins of the heart. In this implementation, the cardiac electrogram signal may be sensed using an electrode positioned in the right ventricle (RV tip electrode, RV ring electrode or RV coil electrode), an electrode positioned within a vein of the left ventricle (LV distal electrode or LV proximal electrode), and/ or electrodes positioned in the right ventricle and the left ventricular vein, for example. The cardiac signal is compared to an activity detection threshold (ADT) which comprises positive and negative thresholds. If the cardiac signal does not exceed 416 the ADT in either the positive or negative direction, then the cardiac response is determined 418 to be a non-captured response. If non-capture is detected, 418 a back up pace may be delivered 420 to one or both ventricles.

If the cardiac signal exceeds 416 the ADT, the cardiac signal morphology is compared to the expected morphology associated with various capture conditions. Cardiac signal features are extracted and compared to detection windows comprising a template associated with a particular type of capture condition. Cardiac signal features may be compared 422 to one or more of a template associated with bi-ventricular capture, a template associated with LV capture and a template associated with RV capture.

In one implementation, the extracted features of the cardiac signal may comprise positive and negative peaks. The amplitude and timing of the cardiac signal peaks may be compared to expected peak amplitudes and peak times associated with capture conditions LV capture, RV capture, and/or bi-ventricular capture.

If the cardiac signal peaks fall within one or more detection windows associated with LV capture, then the capture condition is determined 426 to be LV capture. If the cardiac signal peaks fall within one or more detection windows associated with RV capture, then the capture condition is determined 424 to be RV capture. If the cardiac signal peaks fall within on or more detection windows associated with bi-ventricular capture, then the capture condition is determined 428 to be bi-ventricular capture. If the cardiac signal peaks do not fall within any of the detection windows, or if the cardiac signal peaks fall within multiple detection windows representing different capture conditions, then the capture condition may be determined to be fusion.

If the features of the cardiac signal are consistent with a particular capture template, then the particular capture template may be updated 430 using the features. Methods and systems for updating cardiac pacing response templates are described in commonly owned U.S. Pat. No. 7,574,260, which is hereby incorporated herein by reference.

Figure 5:
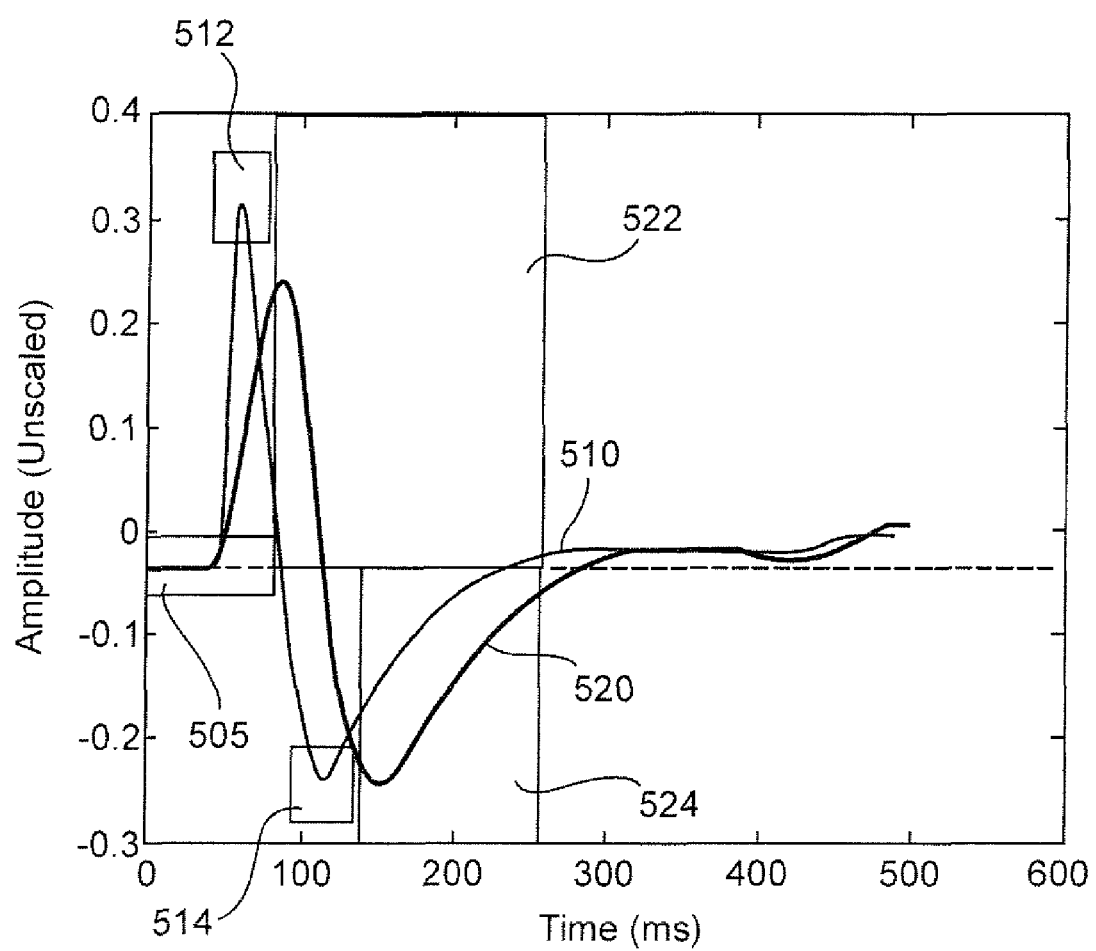
FIG. 5 is a graph illustrating detection windows used for detecting bi-ventricular capture and right ventricle only capture in accordance with embodiments of the invention.

FIG. 5 provides a composite graph of signals representative of bi-ventricular capture 510 and of signals representative of RV capture only (LV non-capture) 520. These signals follow pacing pulses delivered to the right and left ventricles. A signal similar to the bi-ventricular capture signals 510 is produced when the pacing pulses capture both ventricles. A signal similar to the RV capture signals 520 is produced when the pacing pulse delivered to the right ventricle captures the right ventricle and the pacing pulse delivered to the left ventricle does not capture the left ventricle.

Both the bi-ventricular capture signals 510 and the RV capture signals 520 have an initial peak followed by a peak of opposite polarity. However, the signals 510, 520 differ in morphology. As can be seen from FIG. 5, the morphology of the signals 520 associated with RV only capture have slightly wider peak widths and the peaks are delayed in time when compared to the signals 510 associated with bi-ventricular capture.

The morphological differences between signals associated with bi-ventricular capture 510 and signals associated with RV capture 520 can be utilized to discriminate between bi-ventricular capture and RV capture. FIG. 5 illustrates detection windows 512, 514 522, 524 that may be used to discriminate between bi-ventricular capture and RV capture.

First 512 and second 514 bi-ventricular detection windows are used to detect bi-ventricular capture. If the positive peak of a cardiac signal falls within the first bi-ventricular detection window 512 and the negative peak of the cardiac signal falls within the second bi-ventricular detection window 514, then the system determines that both the left and the right ventricles were captured by the pacing pulses.

If the positive peak of the cardiac signal falls in the first RV capture detection window 522 and the negative peak of the cardiac signal falls in the second RV capture detection window 524, then the system determines that the pacing pulse delivered to the right ventricle captured the right ventricle and the pacing pulse delivered to the left ventricle did not capture the left ventricle. If the positive or negative value of the cardiac signal does not exceed the ADT 505, then neither ventricle was captured. If the cardiac signal peaks do not fall within any of the detection windows, or if the cardiac signal peaks fall within multiple detection windows representing the two capture conditions, then the capture condition may be determined to be fusion.

Figure 6:
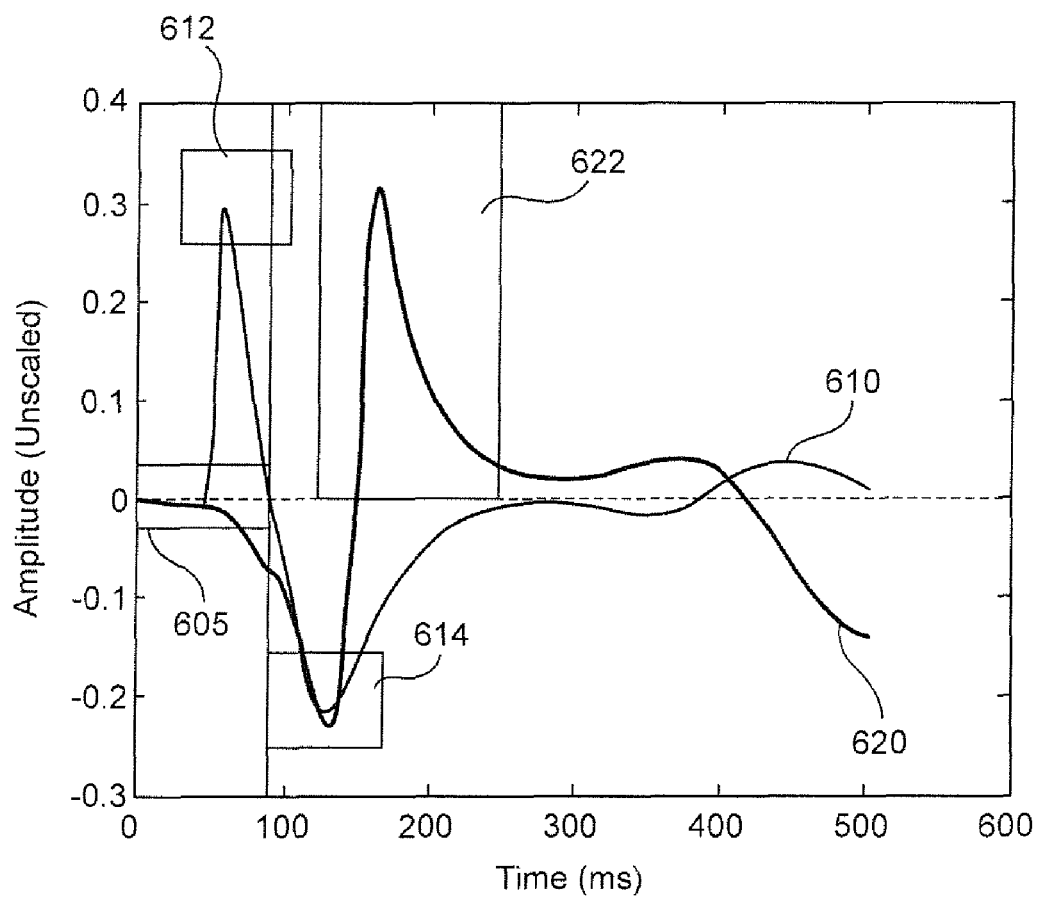
FIG. 6 is a graph illustrating detection windows used for detecting bi-ventricular capture and left ventricle only capture in accordance with embodiments of the invention.

FIG. 6 provides a composite graph of signals representative of bi-ventricular capture 610 and of signals representative of LV capture only (RV non-capture) 620. These signals follow pacing pulses delivered to the right and left ventricles. A signal similar to the bi-ventricular capture signals 610 is produced when the pacing pulses capture both ventricles. A signal similar to the LV capture signals 620 is produced when the pacing pulse delivered to the left ventricle captures the left ventricle and the pacing pulse delivered to the right ventricle does not capture the right ventricle.

As can be seen from FIG. 6, the signals associated with LV capture 620 have peaks that are inverted and delayed in time when compared to the signals associated with bi-ventricular capture 610. The morphological differences between signals associated with bi-ventricular capture and signals associated with LV capture can be utilized to discriminate between bi-ventricular capture and LV capture. FIG. 6 illustrates detection windows 612, 614, 622 that may be used to discriminate between bi-ventricular capture and LV capture.

First 612 and second 614 bi-ventricular detection windows are used to detect bi-ventricular capture. If the positive peak of a cardiac signal falls within the first bi-ventricular detection window 612 and the negative peak of the cardiac signal falls within the second bi-ventricular detection window 614, then the system determines that both the left and the right ventricles were captured by the pacing pulses.

If the positive peak of the cardiac signal falls in the LV capture detection window 622 then the system determines that the pacing pulse delivered to the left ventricle captured the left ventricle and the pacing pulse delivered to the right ventricle did not capture the right ventricle. If the amplitude of the cardiac signal does not exceed the ADT 605, in either the positive or negative direction, then neither ventricle was captured. If the cardiac signal peaks do not fall within any of the detection windows, or if the cardiac signal peaks fall within multiple detection windows representing the two capture conditions, then the capture condition may be determined to be fusion.

By way of example, the processes of the present invention may be used to enhance capture threshold testing to determine a suitable energy for pacing. Determination of a suitable pacing energy may be implemented, for example, by an automatic capture threshold testing procedure executed by an implantable pacemaker/defibrillator or other cardiac rhythm management device. Additionally, automatic capture verification may be used, for example, to monitor capture on a beat-by-beat basis. Automatic capture verification may be used to control back up pacing when a pace pulse delivered to the heart fails to evoke a captured response. These and other applications may be enhanced by the multi-chamber capture approaches of the present invention.

Those skilled in the art will appreciate that reference to a capture threshold testing procedure indicates a method of determining the capture threshold in one or more of the left atrium, the right atrium, both the left atrium and the right atrium, the left ventricle, the right ventricle, and/or both the left ventricle and the right ventricle. In such a procedure, the pacemaker, automatically or upon command, initiates a search for the capture threshold of the selected heart chamber or chambers. The capture threshold is defined as the lowest pacing energy that consistently produces a contraction of the heart chamber.

In one example of an automatic capture threshold procedure, the pacemaker delivers a sequence of pacing pulses to the heart chamber or chambers and detects the cardiac responses to the pace pulses. The energy of the pacing pulses may be decreased in discrete steps until a predetermined number of loss-of-capture events occur. After the predetermined number of loss-of-capture events occur, the pacemaker may increase the stimulation energy in discrete steps until a predetermined number of capture events occur to confirm the capture threshold. A capture threshold test may be performed using the multi-chamber capture detection approaches of the present invention.

Other procedures for implementing capture threshold testing may be utilized. In one example, the pacing energy may be initially set to zero or a relatively low pacing energy and then increased in discrete steps until capture is detected. In another example, the pacing energy may be adjusted according to a binomial search pattern.

Automatic capture threshold determination is distinguishable from automatic capture verification, a procedure that may occur on a beat-by-beat basis during pacing. Automatic capture verification verifies that a delivered pace pulse results in a captured response. When a captured response is not detected following a pace pulse, the pacemaker may deliver a back up safety pace to ensure consistent pacing. The back up pace may be delivered, for example, about 90-110 ms after the initial pace pulse. If a predetermined number of pace pulses delivered during normal pacing do not produce a captured response, the pacemaker may initiate a capture threshold test to determine the capture threshold. Automatic capture verification and back up pacing may be implemented using the multi-chamber capture detection processes of the present invention.

Figure 7:
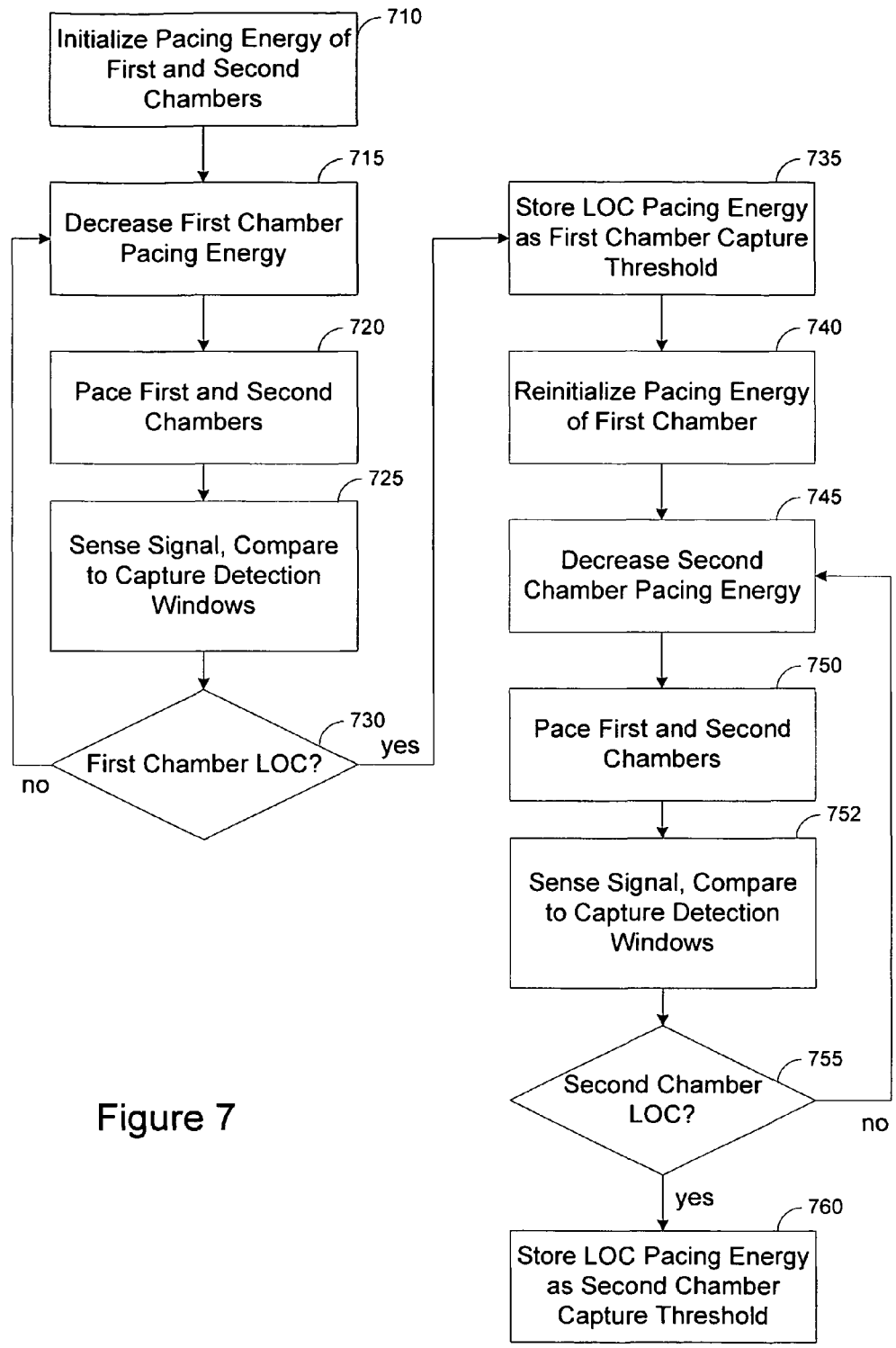
FIG. 7 is a flowchart illustrating a method of performing a multi-chamber capture threshold test in accordance with embodiments of the invention.

FIG. 7 illustrates an automatic capture threshold testing procedure for multi-chamber pacing using multi-chamber capture detection in accordance with approaches of the invention. The pacing energy of first and second heart chambers is initialized 710 to a value exceeding the capture threshold, such as a maximum pacing value. Blocks 715-730 illustrate a method of incrementally decreasing 715 the pacing energy of the first chamber until loss of capture (LOC) occurs 730. After each incremental reduction 715 in pacing energy, the first and second chambers are paced 720. The cardiac signal following the pacing energy is sensed 725 and compared to one or more detection windows associated with expected characteristics of multi-chamber capture and/or second chamber only capture and/or first chamber only capture. If the signal characteristics are consistent with second chamber only capture, then loss of capture of the first chamber is detected 730. The first chamber energy value is stored 735 as the first chamber capture threshold.

The pacing energy of the first chamber is reinitialized 740 to a value exceeding the capture threshold. Blocks 745-755 illustrate a method of incrementally decreasing 745 the pacing energy of the second chamber until loss of capture (LOC) occurs 755. After each incremental reduction 745 in pacing energy, the first and second chambers are paced 750. The cardiac signal following the pacing energy is sensed 752 and compared to one or more detection windows associated with expected characteristics of multi-chamber capture and/or second chamber only capture and/or first chamber only capture. If the signal characteristics are consistent with first chamber only capture, then loss of capture of the second chamber is detected 755. The second chamber energy value is stored 760 as the second chamber capture threshold.

In some embodiments, a first electrogram signal may be used to determine the capture condition and one or more additional electrogram signals may be used to confirm or increase a level of confidence in the capture determination. In some implementations, the first electrogram signal may be sensed using an electrode electrically coupled to a first heart chamber and an additional electrogram signal may be sensed using an electrode electrically coupled to a second heart chamber. In some implementations, the first and additional electrogram signals may be sensed using electrodes electrically coupled to the same chamber.

The processor may evaluate the first and additional cardiac electrogram signals to distinguish capture conditions in various combinations. For example, the processor may evaluate the first signal to discriminate between a first two of right chamber capture only, left chamber capture only, and multi-chamber capture to determine the capture condition. The processor may use an additional signal to distinguish between a second two of right chamber capture only, left chamber capture only, and multi-chamber capture to confirm the capture condition. Distinguishing between other combinations of capture conditions including left chamber capture only, right chamber capture only, multi-chamber capture, non-capture, and fusion for capture confirmation is possible.

Figure 8:
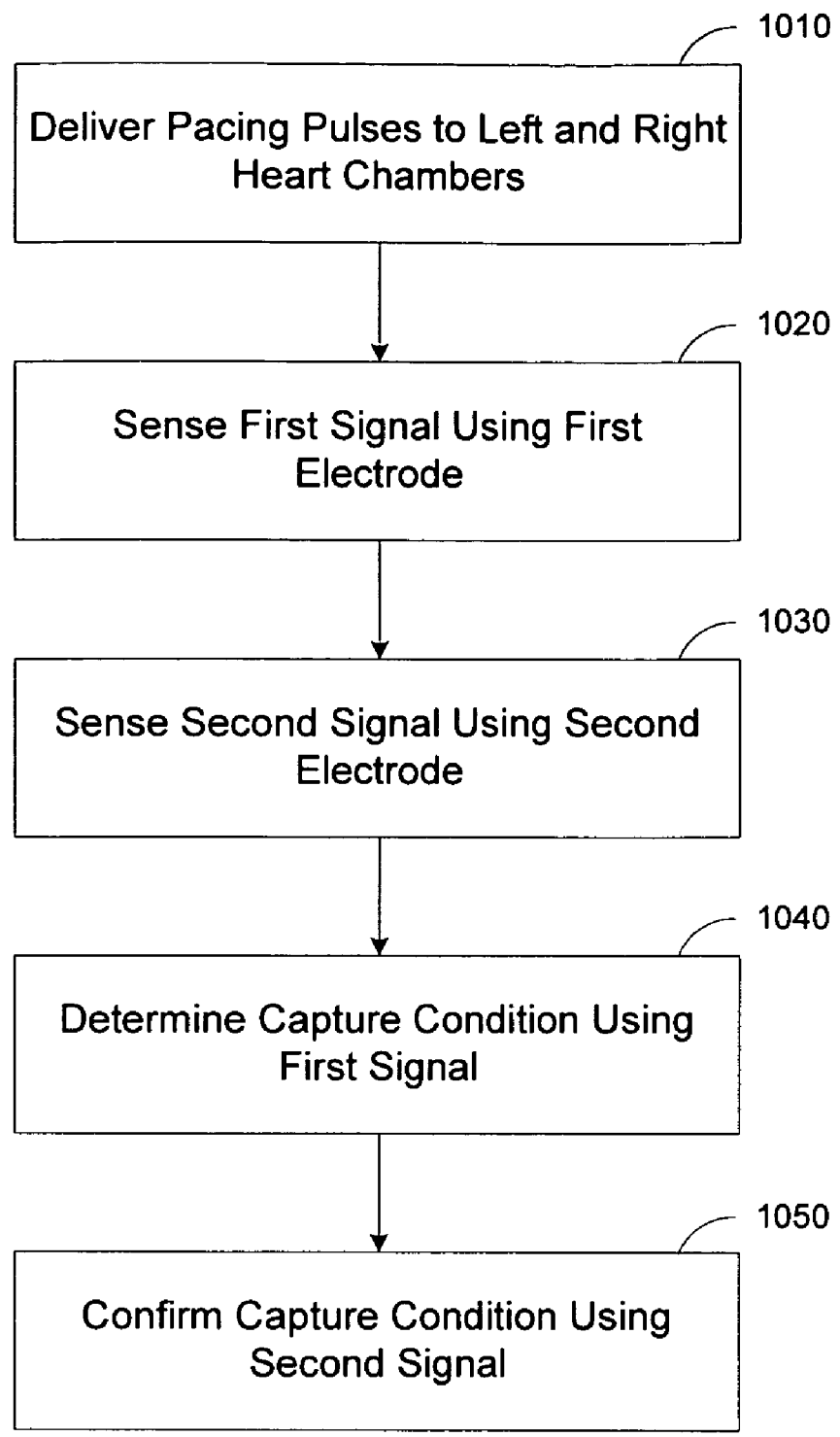
FIG. 8 is a flowchart illustrating a method of confirming the capture condition in accordance with embodiments of the invention.

A process of using an additional electrocardiogram signal for confirming capture determination is illustrated by the flowchart of FIG. 8. Pacing pulses are delivered 1010 to left and right heart chambers during a cardiac cycle. A first electrogram signal is sensed 1020, for example, using an electrode associated with a first heart chamber. A second electrocardiogram is sensed 1030, for example, using an electrode associated with a second heart chamber. The capture condition is determined 1040 using the first signal. The second signal is used to confirm 1050 or increase confidence in the capture condition determination.

Figure 9A:
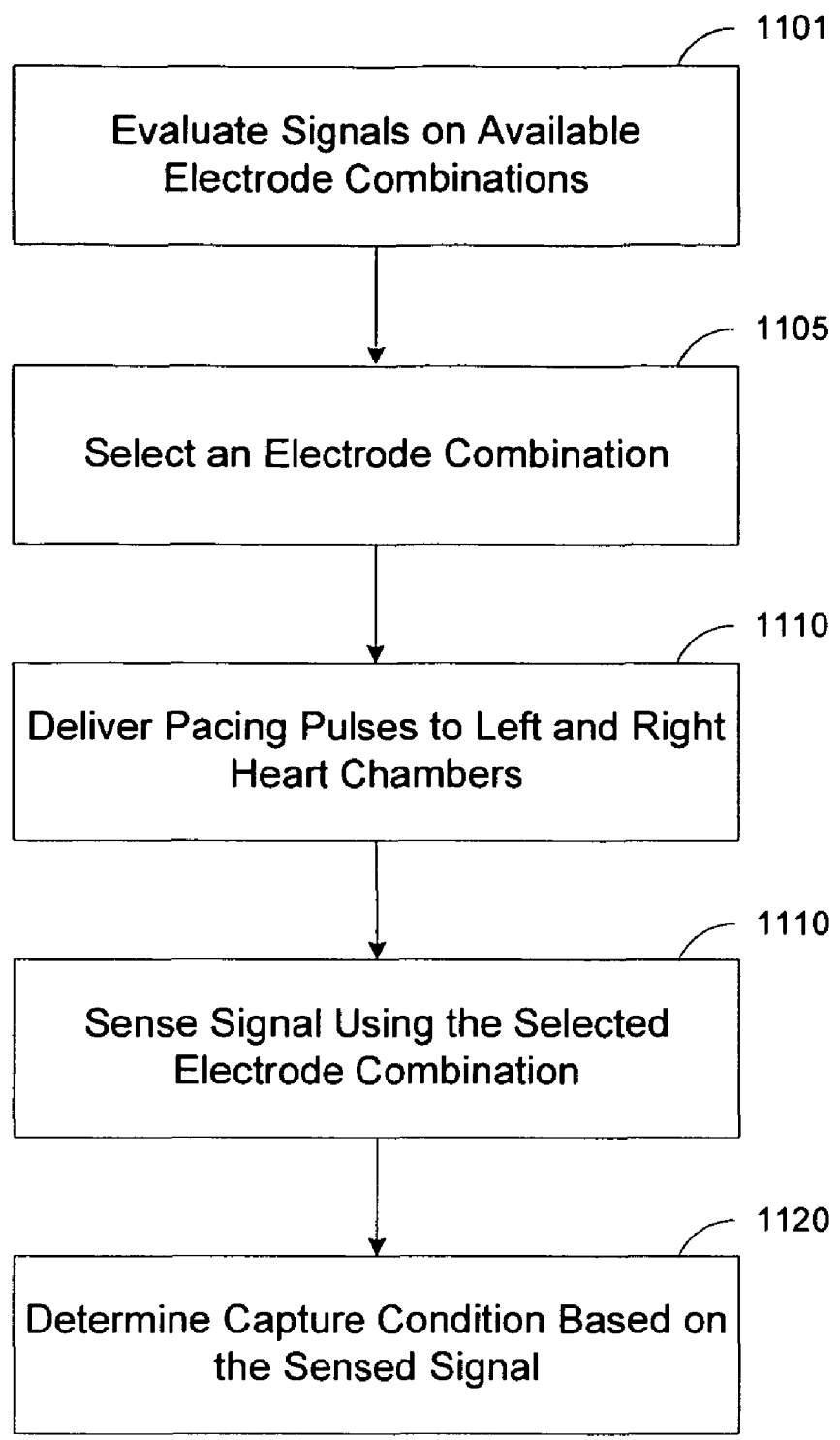
FIGS. 9A and 9B are flowcharts illustrating methods of selecting an electrode for capture sensing in accordance with embodiments of the invention.
Figure 9B:
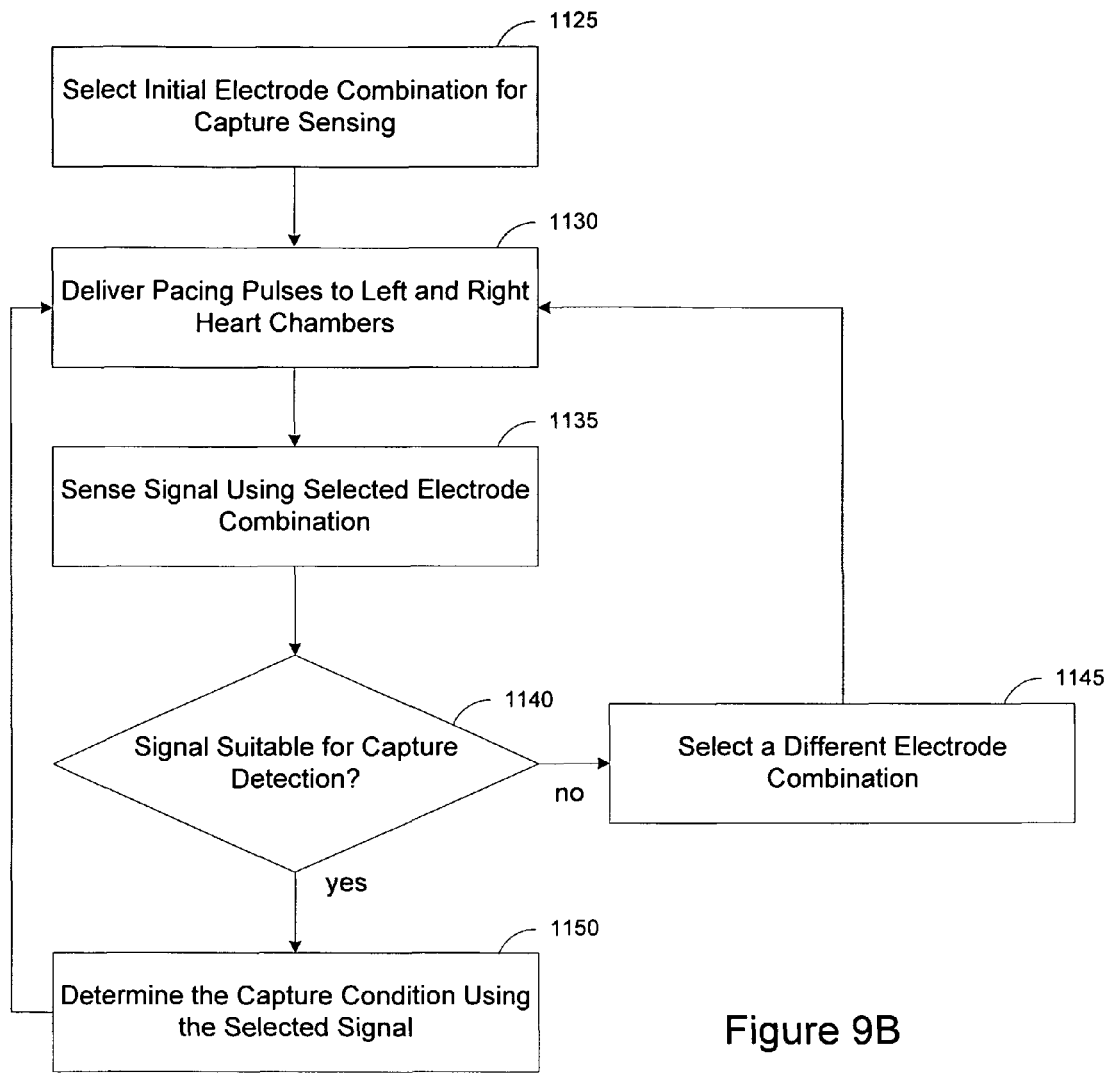

In some embodiments, a selected electrode may be used to determine the capture condition. The selection may be based on parameters of the signal produced using the electrode, including, for example, signal integrity (signal to noise ratio), suitability for capture detection, sensitivity to a particular capture condition, e.g., LV capture or bi-ventricular capture, over sense condition, lead impedance outside a predetermined range, capture amplitude voltage outside a predetermined range, intrinsic amplitude outside a predetermined range, detection of unintended non-cardiac stimulation, failure to detect an expected event and/or other parameters of the signal. FIGS. 9A and 9B are flowcharts illustrating electrode selection processes in accordance with embodiments of the invention.

FIGS. 9A and 9B illustrate methods of selecting capture sensing electrodes for use in automatic capture threshold testing and/or beat to beat automatic capture verification. The process illustrated in FIG. 9A may be particularly suited, for example, for use in connection with an automatic capture threshold test. Prior to beginning the test, the signals produced by available electrode combinations are evaluated 1101 with respect to signal to noise ratio and/or other parameters associated with capture detection suitability as described above. An electrode combination is selected 1105 for capture detection during the test. Pacing pulses are delivered 1110 to left and right heart chambers. The cardiac signal is sensed 1115 using the selected electrode combination. The capture condition is determined 1120 based on characteristics of the sensed signal.

The capture determination process illustrated by the flowchart of FIG. 9B may be used, for example, to select between available electrode combinations in beat to beat automatic capture verification, and/or other capture detection processes. The illustrated process allows the pacemaker to switch between capture sensing electrodes if the signal from a particular electrode combination becomes noisy or produces unreliable capture results. An initial electrode combination is selected 1125 for capture sensing. Pacing pulses are delivered 1130 to the left and right heart chambers. A cardiac electrogram signal is sensed 1135 using the selected electrode combination. If the signal is suitable 1140 for capture detection, e.g., not noisy, minimum signal level, etc., then the capture condition is determined 1150 based on the signal characteristics. If the signal is unsuitable 1140 for capture detection, particularly if the signal is persistently unsuitable, then the system may select 1145 a different electrode combination. Methods and systems for selective use of various electrode combinations to improve capture detection and other pacemaker/defibrillator functions, aspects of which may be utilized in connection with the present invention, are described in commonly owned U.S. Pat. No. 6,493,586 which is incorporated herein by reference.

The components, functionality, and structural configurations depicted herein are intended to provide an understanding of various features and combination of features that may be incorporated in an implantable pacemaker/defibrillator. It is understood that a wide variety of cardiac monitoring and/or stimulation device configurations are contemplated, ranging from relatively sophisticated to relatively simple designs. As such, particular cardiac device configurations may include particular features as described herein, while other such device configurations may exclude particular features described herein.

Various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A method of operating a cardiac rhythm management device in a patient to classify a cardiac response to multi-chamber pacing, comprising:
    delivering a first pacing pulse to a left heart chamber during a cardiac cycle;
    delivering a second pacing pulse to a right heart chamber during the cardiac cycle;
    sensing a cardiac electrogram signal following the first and second pacing pulses;
    determining at least whether (a) a first signal feature of the cardiac signal is disposed within a first detection window, and (b) a second signal feature of the cardiac signal is disposed within a second detection window, at least one of the first and second detection windows being finitely bounded in both time and amplitude; and
    classifying the cardiac response to the first and second pacing pulses as one of bi-chamber capture and a single chamber capture based on the determination of (a) and (b).

2. The method of claim 1, wherein the first signal feature comprises a first peak and the second signal feature comprises a second peak of the cardiac signal.

3. The method of claim 1, wherein both the first and second detection windows are finitely bounded in both time and amplitude.

4. The method of claim 3, wherein the first detection window covers a first amplitude range and the second detection window covers a second amplitude range opposite in polarity to the first amplitude range.

5. The method of claim 3, wherein the first detection window covers a first amplitude range and the second detection window covers a second amplitude range of the same polarity as the first amplitude range.

6. The method of claim 1, wherein the single chamber capture refers to capture of a specific one of the left and right heart chambers.

7. The method of claim 1, wherein the first and second detection windows are non-overlapping.

8. The method of claim 1, wherein the first detection window is associated with bi-chamber capture and the second detection window is associated with a specific single chamber capture.

9. The method of claim 1, wherein the first and second detection windows are both associated with bi-chamber capture.

10. The method of claim 1, wherein the determining step also determines whether (c) a third signal feature of the cardiac signal is disposed within a third detection window, and the classifying step is based also on the determination of (c).

11. The method of claim 1, wherein the first and second pacing pulses are delivered substantially simultaneously.

12. The method of claim 1, wherein the left heart chamber is a left ventricle and the right heart chamber is a right ventricle.

13. An implantable system for classifying a cardiac response to multi-chamber pacing pulses, comprising:
    a pulse delivery system configured to deliver a first pacing pulse to a left heart chamber during a cardiac cycle and a second pacing pulse to a right heart chamber during the cardiac cycle;
    a sensor system configured to sense a cardiac electrogram signal following the first and second pacing pulses; and
    a processor coupled to the sensor system, the processor configured to determine whether (a) a first signal feature of the cardiac signal is disposed within a first detection window, and (b) a second signal feature of the cardiac signal is disposed within a second detection window, the processor further being configured to classify the cardiac response to the first and second pacing pulses as one of bi-chamber capture and a single chamber capture based on the determination of (a) and (b);
    wherein at least one of the first and second detection windows is finitely bounded in both time and amplitude.

14. The system of claim 13, wherein the first signal feature comprises a first peak and the second signal feature comprises a second peak of the cardiac signal.

15. The system of claim 13, wherein both the first and second detection windows are finitely bounded in both time and amplitude.

16. The system of claim 15, wherein the first detection window covers a first amplitude range and the second detection window covers a second amplitude range opposite in polarity to the first amplitude range.

17. The system of claim 15, wherein the first detection window covers a first amplitude range and the second detection window covers a second amplitude range of the same polarity as the first amplitude range.

18. The system of claim 13, wherein the single chamber capture refers to capture of a specific one of the left and right heart chambers.

19. The system of claim 13, wherein the first and second detection windows are non-overlapping.

20. The system of claim 13, wherein the first detection window is associated with bi-chamber capture and the second detection window is associated with a specific single chamber capture.

21. The system of claim 13, wherein the first and second detection windows are both associated with bi-chamber capture.

22. The system of claim 13, wherein the processor is also configured to determine whether (c) a third signal feature of the cardiac signal is disposed within a third detection window, and the processor is configured to classify the cardiac response based on the determination of (a), (b), and (c).

23. The system of claim 13, wherein the pulse delivery system is configured to deliver the first and second pacing pulses substantially simultaneously.

24. The system of claim 13, wherein the left heart chamber is a left ventricle and the right heart chamber is a right ventricle.

* * * * *